United States Patent [19]

Fischell et al.

[11] Patent Number: 5,840,009
[45] Date of Patent: Nov. 24, 1998

[54] RADIOISOTOPE STENT WITH INCREASED RADIATION FIELD STRENGTH AT THE ENDS OF THE STENT

[75] Inventors: Robert E. Fischell, Dayton, Md.; David R. Fischell, Fair Haven, N.J.; Tim A. Fischell, Nashville, Tenn.

[73] Assignee: IsoStent, Inc., Belmont, Calif.

[21] Appl. No.: 567,138

[22] Filed: Dec. 5, 1995

[51] Int. Cl.$^6$ ..................................................... A61N 5/00
[52] U.S. Cl. ................................................................ 600/3
[58] Field of Search .............................. 600/1–8; 606/78, 606/108, 191, 194, 195, 198

[56] References Cited

U.S. PATENT DOCUMENTS 5,059,166  10/1991  Fischell et al. ............................... 600/3
5,176,617  1/1993  Fischell et al. ............................... 600/3

Primary Examiner—John P. Lacyk

[57] ABSTRACT

Disclosed is a radioisotope stent that has increased radioactivity at the end regions of the stent as compared to the stent's central region. To minimize the neointimal hyperplasia that may exist to a greater extent at the ends of a stent that is implanted into an artery of a human body, the amount of radioactivity placed at or near the ends of the stent should be increased as compared to the amount of radioactivity over the remainder of the stent. It is an additional object of this invention to increase the radiation field at the end of a radioisotope stent by placing additional metal surfaces at the ends of the stent so as to have additional surfaces onto which a radioisotope can be placed.

10 Claims, 1 Drawing Sheet

RADIOISOTOPE STENT WITH INCREASED RADIATION FIELD STRENGTH AT THE ENDS OF THE STENT

FIELD OF USE

This invention is in the field of intravascular stents for maintaining vascular patency.

BACKGROUND OF THE INVENTION

Radioisotope stents have been shown to be effective in decreasing neointimal hyperplasia within arteries of laboratory animals thus suggesting a treatment to reduce restenosis in man. By the late 1990's, these stents will be used to prevent vascular closure following balloon angioplasty in human subjects. The radioisotope stents used in animals have had a uniform distribution of a radioisotope that is within the metal of the stent. A uniform distribution of the radioisotope results in a decreased radiation field at the ends of the stent where the highest tendency to form proliferative cell growth can occur.

SUMMARY OF THE INVENTION

To minimize the neointimal hyperplasia that may exist to a greater extent at the ends of a stent, the surface concentration of radioactivity placed at or near the ends of the stent should be increased as compared to the surface concentration of radioactivity over the remainder of the stent.

Therefore, it is an object of this invention to increase the radiation field at the end of a radioisotope stent by placing an increased amount of radioisotope at the ends of the stent.

It is an additional object of this invention to increase the radiation field at the end of a radioisotope stent by placing additional metal surfaces at the ends of the stent so as to have additional surfaces onto which a radioisotope can be placed.

These and other important objects and advantages of this invention will become apparent from the detailed description of the invention and the associated drawings provided herein.

BRIEF DESCRIPTIONS OF THE DRAWINGS

DETAILED DESCRIPTION OF THE DRAWINGS

Figure 1:
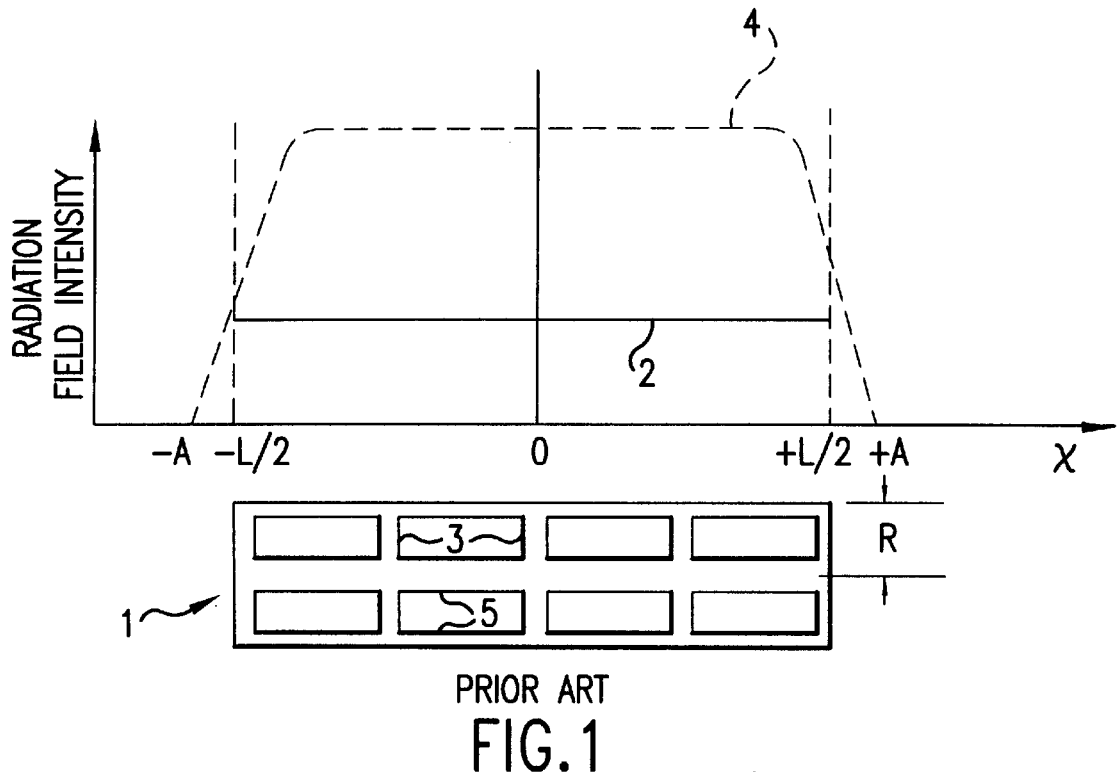
FIG. 1 is a side view of a prior art cylindrical stent having a radioisotope uniformly placed along the length of the stent, and also showing the radiation field strength that results from that uniform distribution of the radioisotope.

FIG. 1 is a side view of a cylindrical stent 1 having a radial dimension R, circumferential rings 3 and longitudinals 5. The stent 1 has a uniform distribution of a radioisotope along its length. This uniform distribution has been used conventionally in prior art radioisotope stents. This type of radioisotope stent is described in detail in U.S. Pat. No. 5,059,166 which is included herein by reference. The solid line 2 in FIG. 1 represents this uniform distribution of radioisotope along the length L of the stent 1 from its left end which is at a distance $x=-L/2$ from the center of the stent 1 to its right end which is at a distance of $x=+L/2$ from the center of the stent 1. The x-axis in FIG. 1 is parallel to the stent's longitudinal axis. The long dashed line 4 in FIG. 1 represents the radiation field intensity or fields strength in human tissue along the surface of a cylinder having a radius of $R+2$ mm which cylinder surrounds the stent 1. The line 4 indicates the radiation field intensity along the surrounding cylinder from $x=-L\backslash 2$ to $x=+L/2$ and also along the surrounding cylindrical surface that extends beyond the ends of the stent 1. A theoretical analysis indicates that the radiation field strength in human tissue along the cylindrical surface surrounding the stent 1 is one-half as great at $x=-L\backslash 2$ and $x=+L/2$ as it is at $x=0$ which is at the longitudinal center of the cylindrical surface surrounding the stent 1. As one moves longitudinally outward on the $R+2$ mm radius surrounding cylindrical surface beyond the ends of the stent 1, the radiation field falls to a negligibly small value at $x=-A$ and $x=+A$.

Figure 2:
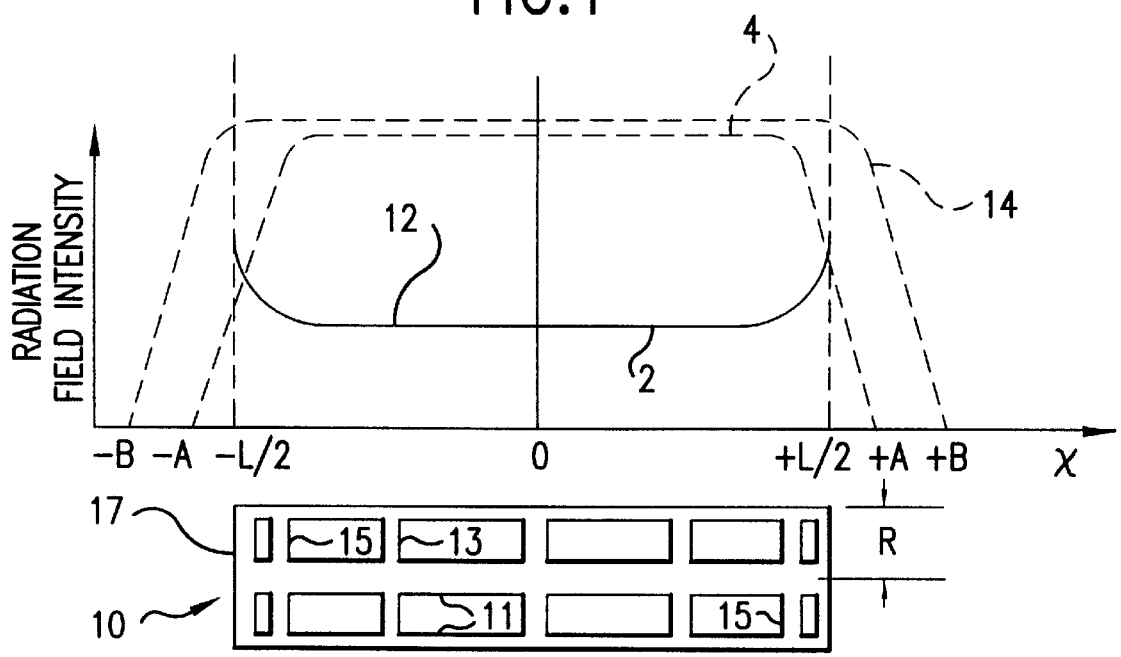
FIG. 2 is a side view of a stent having an increased level of radioactivity near the ends of the stent and also showing the radiation field strength resulting from that non-uniform distribution of the radioactivity compared to prior art stents.

FIG. 2 is a side view of a cylindrical stent 10 of the present invention having longitudinals 11, circumferential rings 13, 15 and 17 and also having an increased concentration of radioisotope placed near the ends of the stent 10. This increased concentration of radioactivity at the ends of the stent is indicated by the solid line 12 of FIG. 2. The resulting field distribution along a cylindrical surface surrounding the stent 1 with a cylindrical radius of $R+2$ mm is shown by the short dashed line 14 in FIG. 2. By increasing the concentration of a radioisotope placed near the ends of the stent 10, the radiation field strength at the stent ends can be made equal to the field strength at the center of the stent 10. Furthermore, the radiation field strength can be made to extend to a greater distance in the x and −x directions beyond the ends of the stent 10. Specifically FIG. 2 shows for comparison the line 4 (from FIG. 1) for a uniform concentration of radioisotope in a stent compared to line 14 which is for the non-uniform distribution of radioisotope shown by line 12 in FIG. 2. It is clearly seen in FIG. 2 that the radiation field strength at the ends of the surrounding cylindrical surface is greater than the field strength from a uniform concentration of radioisotope as shown by line 4 in FIGS. 1 and 2. In fact, at $x=-B$ and $x=+B$ in FIG. 2 it can be seen that the radiation field strength along the surface of the $R+2$ mm radius surrounding cylinder extends for a considerable distance beyond $x=-A$ and $x=+A$. Thus for the same concentration of radioisotope per unit length at the center of the stent for stent 1 and stent 10, a higher level of radioisotope at the ends of stent 10 results in a more uniform radiation field intensity over the length of the surrounding cylinder and also an effective radiation field that extends for a greater distance beyond the ends of the stent 10 and beyond the points $x=-L/2$ and $x=+L/2$ of the surrounding cylinder. Having an increased radiation field at the ends of a stent is useful in reducing proliferative cell growth after the stent is placed inside an artery.

As seen in FIG. 2, the stent 10 may have additional rings 15 placed in near-proximity to the ends of stent 10. The rings 15 provide additional surface area on which to place the radioisotope. Furthermore, the end rings 17 could also be wider so as to provide additional surface onto which additional radioisotope material can be placed. Such additional surfaces can be used to enhance the radiation field intensity at the ends of the stent 10 even if the density of radioisotope per mm of stent surface area is uniform.

It should be understood that the stent 10 can be made radioactive by the ion implantation of a radioisotope into the surface of the metal stent. Furthermore, the beam of an ionized radioisotope can be directed so as to place more of the radioisotope near the ends of the stent as compared to at $x=0$. Typically a beta particle radioisotope such as phosphorous 32 would be ion implanted into the metal of the stent. Gamma or gamma plus beta particle emitting isotopes can also be used with the stent. Furthermore, it may be advantageous to place an anti-thrombogenic coating on the surface of the stent either before (or preferably) after the radioisotope has been ion implanted into the stent. It should also be understood that the stent can be fabricated in a variety of shapes and sizes and could be self-expanding as described in U.S. Pat. No. 4,503,569 or balloon expandable as described in U.S. Pat. No. 4,733,665. Both of the aforementioned patents are included herein by reference. Still further, the radioisotope could be electrolytically plated onto the stent instead of using ion implantation.

The radioisotope could also be plated onto the stent by vapor deposition. It is also conceived that the distribution of the radioisotope at the ends of stent can have a different shape than that shown by line 12 in FIG. 2. Specifically, some comparatively short distance at the end of stent could have an increased amount of radioisotope per unit length compared to the stent's center portion, but that higher radioisotope amount per unit length could be uniform near the end of the stent.

Various other modifications, adaptations, and alternative designs are of course possible in light of the above teachings. Therefore, it should be understood at this time that within the scope of the appended claims, the invention may be practiced otherwise than as specifically described herein.

What is claimed is:

1. A radioisotope stent comprising a generally cylindrical, thin-walled, metal structure, the stent having an end region near each end of the stent and a central region located generally at the longitudinal center of the stent, the stent including a radioactive material which is a radioisotope, the radioisotope being fixedly joined to the metal of the stent, the stent also having a greater amount of a radioisotope per unit length of the stent at the end regions of the stent compared to a lesser amount of radioisotope per unit length at the central region of the stent.

2. The stent of claim 1 wherein the amount of radioisotope per unit length of stent continuously increases towards the ends of the stent from some point between the center of the stent and the end of the stent, the amount of radioisotope per unit length of stent reaching a maximum amount of radioisotope per unit length at the ends of stent.

3. The stent of claim 1 wherein the radioisotope that is fixedly joined to the stent is a beta-particle emitting radioisotope.

4. The stent of claim 3 wherein the radioisotope is phosphorous 32.

5. The stent of claim 1 wherein the stent is coated with an antithrombogenic coating.

6. The stent of claim 1 wherein the stent is adapted to be expanded by an inflatable balloon.

7. The stent of claim 1 wherein the stent is adapted to be self-expanding.

8. The stent of claim 1 wherein the metal of the stent has a surface and at least some of the radioisotope is plated onto the surface of the stent to form a surface coating.

9. The stent of claim 1 wherein metal of the stent has a surface and the stent has at least some of the radioisotope ion implanted into the metal of the stent to form a radioactive stent in which the ions of the radioisotope are buried just beneath the surface of the stent.

10. The stent of claim 1 wherein the end region of the stent has more surface area per unit length of the stent as compared to the surface area per unit length of the stent at the stent's central region, the stent having a generally uniform amount of radioisotope per unit surface area of the stent thus providing an increased amount of radioisotope per unit length of the stent at the stent's end regions.

* * * * *